(12) United States Patent
Franco et al.

(10) Patent No.: US 12,102,650 B2
(45) Date of Patent: Oct. 1, 2024

(54) ANHYDROUS ANTIMICROBIAL TOPICAL FORMULATIONS AND METHODS OF USE THEREOF

(71) Applicant: NSC—NANO SONO COOPERATION LTD, Yokneam Illit (IL)

(72) Inventors: Ariel Antonio Franco, Yokneam Illit (IL); Rajashekharayya A. Sanguramath, Yokneam Illit (IL)

(73) Assignee: NSC-NANO SONO COOPERATION LTD, Yokneam, IL (US)

( * ) Notice: Subject to any disclaimer, the term of this patent is extended or adjusted under 35 U.S.C. 154(b) by 197 days.

(21) Appl. No.: 17/373,781

(22) Filed: Jul. 13, 2021

(65) Prior Publication Data
US 2022/0008461 A1  Jan. 13, 2022

Related U.S. Application Data

(60) Provisional application No. 63/050,933, filed on Jul. 13, 2020.

(51) Int. Cl.
| | |
|---|---|
| A61K 33/34 | (2006.01) |
| A61K 9/00 | (2006.01) |
| A61K 9/06 | (2006.01) |
| A61K 33/00 | (2006.01) |
| A61K 33/06 | (2006.01) |
| A61K 33/242 | (2019.01) |
| A61K 33/30 | (2006.01) |
| A61K 33/38 | (2006.01) |
| A61K 47/06 | (2006.01) |
| A61K 47/10 | (2017.01) |
| A61K 47/14 | (2017.01) |
| A61K 47/22 | (2006.01) |
| A61K 47/26 | (2006.01) |
| A61K 47/69 | (2017.01) |
| A61P 31/02 | (2006.01) |

(52) U.S. Cl.
CPC ............ *A61K 33/34* (2013.01); *A61K 9/0014* (2013.01); *A61K 9/06* (2013.01); *A61K 33/00* (2013.01); *A61K 33/06* (2013.01); *A61K 33/242* (2019.01); *A61K 33/30* (2013.01); *A61K 33/38* (2013.01); *A61K 47/06* (2013.01); *A61K 47/10* (2013.01); *A61K 47/14* (2013.01); *A61K 47/22* (2013.01); *A61K 47/26* (2013.01); *A61K 47/6935* (2017.08); *A61P 31/02* (2018.01)

(58) Field of Classification Search
CPC ...................................................... A61P 31/02
See application file for complete search history.

(56) References Cited

U.S. PATENT DOCUMENTS

| | | | |
|---|---|---|---|
| 2008/0063607 A1 | 3/2008 | Tamarkin | |
| 2008/0213198 A1 | 9/2008 | Lintner | |
| 2008/0253973 A1* | 10/2008 | Eini | ......................... A61K 9/12 |
| | | | 424/47 |
| 2008/0299220 A1* | 12/2008 | Tamarkin | ............... A61K 33/00 |
| | | | 424/600 |

OTHER PUBLICATIONS

Archana R. Deokar et al, A topical antibacterial ointment made of Zn-doped copper oxide nanocomposite, J Nanopart Res (2016) 18:218 (Year: 2016).*
Marilena Carbone et al, Antimicrobial power of Cu/Zn mixed oxide nanoparticles to *Escherichia coli*, Environmental Nanotechnology, Monitoring & Management 7 (2017) 97-102 (Year: 2017).*
Tahseen H. Mubarak, et al.,"Preparation and study structure properties of Zinc-Copper ferrite (ZnOX CuO 1-x Fe 2 O 3) nanoparticles", IOSR Journal of Applied Physics, vol. 9, No. 6, Nov. 21, 2017.

* cited by examiner

*Primary Examiner* — Mark V Stevens
*Assistant Examiner* — Alparslan Asan
(74) *Attorney, Agent, or Firm* — JMB Davis Ben-David

(57) ABSTRACT

Described herein are anhydrous antimicrobial topical formulations including metal nanoparticles and terpenes. Methods of use of the described formulations in wound treatment are also described.

3 Claims, 1 Drawing Sheet

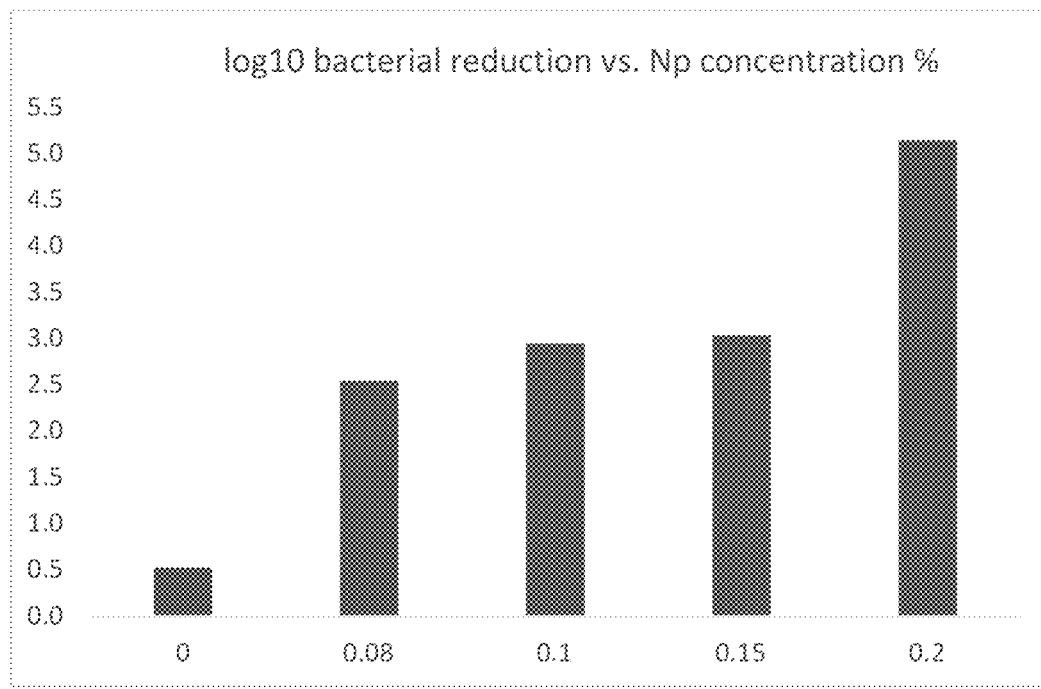

ANHYDROUS ANTIMICROBIAL TOPICAL FORMULATIONS AND METHODS OF USE THEREOF

CROSS REFERENCE TO RELATED APPLICATIONS

Benefit is claimed to U.S. Provisional Patent Application No. 63/050,933, filed Jul. 13, 2020, the contents of which are incorporated by reference herein in their entirety.

FIELD

This disclosure relates to anhydrous antimicrobial topical formulations including metal nanoparticles and terpenes. Methods of use of the described formulations in wound treatment are also described.

BACKGROUND

Wound healing follows a process of four overlapping phases of hemostasis, inflammation, proliferation, and remodeling. This regular healing process can be impaired, and wounds failing to heal within 12 weeks period are considered to be chronic wounds. Often, prolonged inflammation and persistent microbial infection, including biofilm growth, are the critical challenges for effective treatment of chronic wounds. Although antibiotics can be effective against such infections, inappropriate and excessive use of antibiotics has led to a rapid emergence of resistant strains. Moreover, biofilms are often intrinsically drug-resistant. In addition to infection, compromised vasculature around the wound site can prevent the delivery of systemically administered antibiotics. To address these treatment challenges, wound dressings incorporating antibacterial additives such as metal and metal oxide are rapidly gaining importance.

Unlike conventional antibiotics, the bacterial resistance to metal and metal oxide nanoparticles is extremely rare. However, production of a stable ointment that includes metal or metal oxide nanoparticles and provides a broad-spectrum antimicrobial effect remains a continuing challenge.

SUMMARY

Provided herein is an anhydrous antimicrobial topical ointment that includes at least one polyethylene glycol from about 84 to about 99.75 wt %; a non-ionic surfactant from about 0.05 to about 2.0 wt %; a lipid material from about 0.1 to about 5.0 wt %; wherein the lipid material is a fatty acid, an oil, a wax, a triglyceride, or combinations thereof; at least one terpene from about 0.05 to about 2.0 wt %; a metal nanoparticle or nanocomposite from about 0.05 to about 2.0 wt %; and glycerin from 0 to about 5 wt %.

In particular embodiments, the at least one polyethylene glycol is from about 87 to about 98.5 wt %; the non-ionic surfactant is from about 0.5 to about 1.5 wt %; the lipid material is from about 0.4 to about 4.0 wt %; the at least one terpene is from about 0.5 to about 1.5 wt %; and the metal nanoparticle or nanocomposite is from about 0.1 to about 1.0 wt %.

In other embodiments, the at least one polyethylene glycol is from about 90.5 to about 98.0 wt %; the non-ionic surfactant is from about 0.7 to about 1.25 wt %; the lipid material is from about 0.5 to about 1.0 wt %; the at least one terpene is from about 0.7 to about 1.25 wt %; and the metal nanoparticle or nanocomposite is from about 0.1 to about 0.5 wt %.

In one embodiment, the at least one polyethylene glycol comprises at least two polyethylene glycols of different molecular weights, wherein the combined wt % of the lower molecular weight polyethylene glycol is greater than the combined wt % of the higher molecular weight polyethylene glycol.

In a particular embodiment, the at least one polyethylene glycol (PEG) is at least two PEGs including PEG-400 and PEG-4000.

In some embodiments, the non-ionic surfactant is selected from a group consisting of TWEEN-20, TWEEN-80, ceteareth-20, SPAN-85, and combinations thereof.

In a particular embodiment, the non-ionic surfactant is TWEEN-80.

In some embodiments, the lipid material comprises octyldodecanol, almond oil, isopropyl myristate, caprylic/capric triglyceride, or combination thereof.

In other embodiments, the lipid material comprises isopropyl myristate and/or caprylic/capric triglyceride.

In still other particular embodiments, the at least one terpene is selected from a group consisting of myrcene, limonene, α-pinene, β-pinene, α-bisabolol, eucalyptol, trans-nerolidol, borneol, geraniol, cymene, eugenol, and combinations thereof, and can in certain embodiments be selected from a group consisting of α-bisabolol, borneol, eugenol, and combinations thereof, and still more particularly the terpene is α-bisabolol.

In some embodiments, the metal nanoparticle includes gold, silver, titanium, copper, zinc, magnesium, or combinations thereof. In other embodiments, the metal nanoparticle is a metal oxide nanoparticle or nanocomposite including zinc oxide, silver oxide, titanium oxide, copper oxide/zinc oxide, magnesium oxide, or combinations thereof.

In still further embodiment, the metal nanoparticle or nanocomposite is a nanocomposite comprising $CuO_{(1-x)}ZnO_x$.

In other embodiments, the metal nanoparticle or nanocomposite is provided in the formulation as a PEG-metal nanoparticle or nanocomposite suspension.

In a particular embodiment, the anhydrous antimicrobial topical ointment includes about 76.2 wt % polyethylene glycol (PEG)-400; about 20 wt % PEG-4000; about 0.8 wt % TWEEN-80 surfactant; about 1 wt % capric triglycerides; about 1 wt % α-bisabolol; and about 1 wt % $CuO_{(1-x)}ZnO_x$, wherein the $CuO_{(1-x)}ZnO_x$ is provided in a suspension of PEG-400, particularly up to 25% of the PEG-400 in the ointment.

Also described herein is an antimicrobial composition for use in methods of wound treatment comprising any of the described embodiments of the anhydrous antimicrobial topical ointment. In particular embodiments the antimicrobial composition consists of the anhydrous antimicrobial topical ointment. In other embodiments, the composition includes the anhydrous antimicrobial topical ointment in combination with a pharmaceutically acceptable carrier, excipient, or salt, suitable for use with an ointment composition.

In particular embodiments, the described methods of wound treatment include administering the composition to a subject in need thereof by contacting a wound with the composition, thereby inhibiting microbial growth and treating the wound.

In particular embodiments of described uses and methods of treatment, the wound to be or under treatment is an incision; acute or chronic surface injury, burn, diabetic ulcer, topical mycosis, infected eczema, and infectious acne.

In particular embodiments, the composition is inhibitory or microbicidal to antibiotic-resistant microbes. In other embodiments, the composition is an antioxidant, anti-inflammatory, and regenerative composition.

In still further embodiments, the described ointment formulations can be use in treating or preventing an infection present in or on a wound, such as an antibiotic resistant infection.

The foregoing and other objects, features, and advantages will become more apparent from the following detailed description, which proceeds with reference to the accompanying FIGURES.

BRIEF DESCRIPTION OF THE DRAWINGS

FIG. 1 is a graph showing logarithm of reduction in microbial growth versus the concentration of nanoparticles, according to the standard ASTM E2315, against *Staphylococcus aureus* ATCC, at 2 hours contact time in FBS 5%.

DETAILED DESCRIPTION

I. Terms

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all molecular weight or molecular mass values, are approximate, and are provided for description. Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example." The term "wt %" is equivalent to "w/w." The term "about" indicates that a given value can be +/-up to 5% of that noted. In case of conflict, the present specification, including explanations of terms, will control. In addition, all the materials, methods, and examples are illustrative and not intended to be limiting.

Administration: The introduction of a composition into or onto a subject by a chosen route. For example, the described polymer-nanoparticle composite compounds can be administered locally at a wound site by any method known to the art of contacting a surface with a compound.

Antimicrobial agent: A compound that inhibits, prevents, or eradicates the growth, replication, spread or activity of a microorganism. In a particular embodiment, an antimicrobial agent is a metal or metal oxide nanoparticle component of the described polymer-nanoparticle composite compounds. When used generally, an antimicrobial agent can inhibit, prevent, or eradicate the growth and spread of living microbes such as bacteria and fungi. Similarly, an antimicrobial agent can also inhibit the viability of a viral particle to infect and successfully replicate within a host, thereby eradicating its presence from the host. A microbe may be inhibited when its presence or activity is decreased by at least 10%, at least 20%, at least 30%, at least 50%, at least 80%, at least 100% or at least 250% or more as compared to a microbe that has not been contacted with the compound.

Contacting: Placement in direct physical association; including contact of a surface by a composition both in solid and liquid forms. Contacting can occur in vivo by administering to a subject.

Composite: A material composed of two or more constituent parts, which are generally structurally and physically distinct. A nanocomposite material is of a size in the nanometer (nm) range, typically 1 to 1000 nm, and can in certain embodiments be composed of nanoparticles of a size also in the nm range.

Doped (metal oxide): A metal oxide compound into which impurities are intentionally introduced. A co-doped composite compound contains multiple impurities.

Effective amount of a compound: A quantity of compound sufficient to achieve a desired effect. In a therapeutic context, a therapeutically effective amount of a compound is that amount to achieve a desired effect in a subject being treated. For example, the therapeutically effective amount of the described polymer-nanoparticle composite compound in a solid matrix (such as a bandage) will be the amount necessary to enhance/assist hemostasis and provide antimicrobial effects when brought into contact with a wound.

Pharmaceutically acceptable carriers, salts, excipients: The pharmaceutically acceptable carriers, salts, and excipients useful in this disclosure are conventional. *The Science and Practice of Pharmacy*, Adeboye Adejare, Ed., 23rd Edition (2020), describes compositions and formulations suitable for pharmaceutical delivery of the compounds herein disclosed. In general, the nature of the carrier, salt, and excipient will depend on the particular mode of administration being employed, for example for use as or with a topical agent in an ointment, cream, or similar suspension, such as the ointment formulation described herein.

Subject: Living multi-cellular organisms, including vertebrate organisms, a category that includes both human and non-human mammals. Used interchangeably with patient.

Wound: An injury to living tissue which can, but does not require breaking skin or bleeding. Particular non-limiting examples of wounds include bruises, burns, and cuts (of varying depths and severity). Wounds can be unintentional, such as resulting from a fall, but can also be intentional, such as a result of surgery or other medical procedure. As used herein, a "chronic wound" is any wound that has not healed after 12 weeks following injury. An "acute wound" is any wound prior to its classification as a chronic wound. The ointment formulations described herein can treat chronic as well as acute wounds.

Wound dressing: Any covering of any material used to cover a wound. In particular embodiments, wound dressings can be of natural or synthetic fabrics. In other embodiments, wound dressings can be films composed of or including the described compositions. In particular embodiments, a wound dressing does not include any active material. In other embodiments, a wound dressing includes the described compositions, alone, or with other therapeutic agents, such as standard analgesic and anti-inflammatory drugs.

II. Ointment Formulation

Metal nanoparticle compositions have been shown to provide a robust broad-spectrum antimicrobial effect. To provide this therapeutic benefit in wound care, it is advantageous to include such antimicrobial compounds in an ointment composition. However, as demonstrated below, conventional ointment formulations that include a metal oxide nanocomposite were observed to not provide an antimicrobial effect. The current disclosure relates to a newly-developed ointment formulation that retains the antimicrobial activity of a metal or metal oxide nanoparticle or nanocomposite, yet is also stable and spreadable. The ointment formulation described herein includes at least one polyethylene glycol; a surfactant; a lipid material; at least one terpene; a metal oxide nanoparticle; and glycerin. The described ointment is antimicrobial, moisturizing, anti-inflammatory, moisturizing, and analgesic. Moreover, with the inclusion of terpene compounds, such as α-bisabolol, the described formulation is also anti-inflammatory, antioxidant, and regenerative. These combined properties help to treat and prevent infections and heal wounds and shorten the time for wound healing.

Polyethylene Glycol

The ointment formulation comprises at least one polyethylene glycol (PEG), such as at least two, at least three, or at least four PEGs. In some embodiments, the ointment formulation comprises two different polyethylene glycols of different molecular weights. In general, the amount of the lower molecular weight PEG is greater than the higher molecular weight PEG. This specific combination of PEGs allows a spreadable and non-occlusive matrix to for the ointment formulation for topical applications. Non-limiting examples of suitable polyethylene glycols include PEG400, PEG800, PEG3000, PEG3350, PEG4000, PEG8000, or combinations thereof. In some embodiments, the polyethylene glycols comprise PEG300, PEG600, PEG3365, PEG4000, PEG8000, or combinations thereof. In a particular embodiment, two PEGs are present in the formulation, and are a combination of PEG400 and PEG4000.

In general, the amount of the at least one polyethylene glycol in the total ointment formulation may range from about 84 wt % to about 99.75 wt %. In various embodiment, the amount of the at least one polyethylene glycol in the total ointment formulation may range from about 84 wt % to about 99.75 wt %, or from 87 to 98.5 wt %, or from 90.5 to about 98.0 wt %. In one preferred embodiment, the amount of the at least one polyethylene glycol in the total ointment formulation is about 97 wt %.

In some embodiments, at least two PEGs are present in the formulation. In particular embodiments of such formulations, the relative amount of the lower molecular weigh PEG is greater than the higher molecular weight PEG. In Particular embodiments the ratio of the two PEGs (low:high) is 1.25:1, 1.5:1, 2:1, 3:1, 4:1, 5:1, 6:1, 7:1, 8:1, 9:1. 10:1 and sub-increments therein.

Non-Ionic Surfactant

The ointment composition comprises at least one surfactant, which stabilizes and provides homogeneity to the formulation. In general, the surfactant is a pharmaceutically acceptable non-ionic surfactant, which can be a pharmaceutically acceptable nonionic polymeric surfactant. Polymeric surfactants include, not limited to, a graft copolymer of a poly(methyl methacrylate) backbone with multiple (at least one) polyethylene oxide (PEO) side chain, polyhydroxystearic acid, an alkoxylated alkyl phenol formaldehyde condensate, a polyalkylene glycol modified polyester with fatty acid hydrophobes, a polyester, semi-synthetic derivatives thereof, or combinations thereof.

Additional suitable surfactants for use in the described ointment formulations include but are not limited to, ethoxylated nonylphenol comprising 9 to 10 units of ethyleneglycol, ethoxylated undecanol comprising 8 units of ethyleneglycol, polyoxyethylene (20) sorbitan monolaurate, polyoxyethylene (20) sorbitan monopalmitate, polyoxyethylene (20) sorbitan monostearate, polyoxyethylene (20) sorbitan monooleate (i.e., polysorbate 80), sorbitan monolaurate, sorbitan monopalmitate, sorbitan monostearate, sorbitan monooleate, ethoxylated hydrogenated ricin oils, sodium laurylsulfate, a diblock copolymer of ethyleneoxyde and propyleneoxyde, ethylene oxide-propylene oxide block copolymers, and tetra-functional block copolymers based on ethylene oxide and propylene oxide, glyceryl monoesters, glyceryl caprate, glyceryl caprylate, glyceryl cocate, glyceryl erucate, glyceryl hydroxysterate, glyceryl isostearate, glyceryl lanolate, glyceryl laurate, glyceryl linolate, glyceryl myristate, glyceryl oleate, glyceryl PABA, glyceryl palmitate, glyceryl ricinoleate, glyceryl stearate, glyceryl thiglycolate, glyceryl dilaurate, glyceryl dioleate, glyceryl dimyristate, glyceryl disterate, glyceryl sesuioleate, glyceryl stearate lactate, polyoxyethylene cetyl/stearyl ether, polyoxyethylene cholesterol ether, polyoxyethylene laurate or dilaurate, polyoxyethylene stearate or distearate, polyoxyethylene fatty ethers, polyoxyethylene lauryl ether, polyoxyethylene stearyl ether, polyoxyethylene myristyl ether, a steroid, cholesterol, betasitosterol, bisabolol, fatty acid esters of alcohols, isopropyl myristate, aliphati-isopropyl n-butyrate, Isopropyl n-hexanoate, Isopropyl n-decanoate, Isopropyl palmitate, octyldodecyl myristate, alkoxylated alcohols, alkoxylated acids, alkoxylated amides, alkoxylated sugar derivatives, alkoxylated derivatives of natural oils and waxes, polyoxyethylene polyoxypropylene block copolymers, nonoxynol-14, PEG-8 laurate, PEG-6 Cocoamide, PEG-20 methylglucose sesquistearate, PEG-40 lanolin, PEG-40 castor oil, PEG-40 hydrogenated castor oil, polyoxyethylene fatty ethers, glyceryl diesters, polyoxyethylene stearyl ether, polyoxyethylene myristyl ether, and polyoxyethylene lauryl ether, glyceryl dilaurate, glyceryl dimystate, glyceryl distearate, semi-synthetic derivatives thereof, or mixtures thereof.

Additional surfactants for use in the described ointments include, without limit, non-ionic lipids, such as glyceryl laurate, glyceryl myristate, glyceryl dilaurate, glyceryl dimyristate, semi-synthetic derivatives thereof, and mixtures thereof.

In additional embodiments, the at least one surfactant can be a polyoxyethylene fatty ether having a polyoxyethylene head group ranging from about 2 to about 100 groups, or an alkoxylated alcohol having the structure R5-(OCH2 CH2)y-OH, wherein R5 is a branched or unbranched alkyl group having from about 6 to about 22 carbon atoms and y is between about 4 and about 100, and preferably, between about 10 and about 100.

In a different embodiment, the at least one surfactant may be an alkoxylated alcohol which is an ethoxylated derivative of lanolin alcohol. Preferably, the ethoxylated derivative of lanolin alcohol is laneth-10, which is the polyethylene glycol ether of lanolin alcohol with an average ethoxylation value of 10.

In other particular embodiments, nonionic surfactants include, without limit, an ethoxylated surfactant, an alcohol ethoxylated, an alkyl phenol ethoxylated, a fatty acid ethoxylated, a monoalkaolamide ethoxylated, a sorbitan ester ethoxylated, a fatty amino ethoxylated, an ethylene oxide-propylene oxide copolymer, bis(polyethylene glycol bis[imidazoyl carbonyl]), nonoxynol-9, Bis(polyethylene glycol bis[imidazoyl carbonyl]), BRIJ 35, BRIJ 56, BRIJ 72, BRIJ 76, BRIJ 92V, BRIJ 97, BRIJ 58P, CREMOPHOR EL, decacthylene glycol monododecyl ether, N-decanoyl-N-methylglucamine, n-decyl alpha-D-glucopyranoside, decyl beta-D-maltopyranoside, n-dodecanoyl-N-methylglucamide, n-dodecyl alpha-D-maltoside, n-Dodecyl beta-D-maltoside, n-dodecyl beta-D-maltoside, heptaethylene glycol monodecyl ether, heptaethylene glycol monododecyl ether, heptaethylene glycol monotetradecyl ether, n-hexadecyl beta-D-maltoside, hexaethylene glycol monododecyl ether, hexaethylene glycol monohexadecyl ether, hexacthylene glycol monooctadecyl ether, hexaethylene glycol monotetradecyl ether, igepal CA-630, igepal CA-630, methyl-6-O—(N-heptylcarbamoyl)-alpha-D-glucopyranoside, nonaethylene glycol monododecyl ether, N-nonanoyl-N-methylglucamine, N-nonanoyl-N-methylglucamine, octacthylene glycol monodecyl ether, octaethylene glycol monododecyl ether, octaethylene glycol monohexadecyl ether, octacthylene glycol monooctadecyl ether, octaethylene glycol monotetradecyl ether, octyl-beta-D-glucopyranoside, pentaethylene glycol monodecyl ether, pentaethylene glycol monododecyl ether, pentaethylene glycol monohexadecyl ether, pentaethylene glycol monohexyl ether, pentaethylene glycol monooctadecyl ether, pentaethylene glycol monooctyl ether, polyethylene glycol diglycidyl ether, polyethylene glycol ether W-1, polyoxyethylene 10 tridecyl ether, polyoxyethylene 100 stearate, polyoxyethylene 20 isohexadecyl ether, polyoxyethylene 20 oleyl ether, polyoxyethylene 40 stearate, polyoxyethylene 50 stearate, polyoxyethylene 8 stearate, polyoxyethylene bis(imidazolyl carbonyl), polyoxyethylene 25 propylene glycol stearate, saponin from quillaja bark, SPAN 20, SPAN 40, SPAN 60, SPAN 65, SPAN 80, SPAN 85, Tergitol, Type 15-S-12, tergitol, Type 15-S-30, tergitol, Type 15-S-5, tergitol, Type 15-S-7, tergitol, Type 15-S-9, tergitol, Type NP-10, tergitol, Type NP-4, tergitol, Type NP-40, tergitol, Type NP-7, tergitol, Type NP-9, tergitol, Tergitol, Type TMN-10, tergitol, Type TMN-6, tetradecyl-beta-D-maltoside, tetraethylene glycol monodecyl ether, tetraethylene glycol monododecyl ether, tetraethylene glycol monotetradecyl ether, triethylene glycol monodecyl ether, tricthylene glycol monododecyl ether, triethylene glycol monohexadecyl ether, triethylene glycol monooctyl ether, tricthylene glycol monotetradecyl ether, TRITON CF-21, TRITON CF-32, TRITON DF-12. TRITON DF-16, TRITON GR-5M. TRITON QS-15, TRITON QS-44, TRITON X-100, TRITON X-102, TRITON X-15. TRITON X-151, TRITON X-200. TRITON X-207. TRITON X-100, TRITON X-114, TRITON X-165, TRITON X-305, TRITON X-405, TRITON X-45, TRITON X-705-70, TWEEN 20, TWEEN 21, TWEEN 40, TWEEN 60, TWEEN 61, TWEEN 65, TWEEN 80, TWEEN 81, TWEEN 85, tyloxapol, n-undecyl beta-D-glucopyranoside, semi-synthetic derivatives thereof, or combinations thereof.

In some embodiments, the nonionic surfactant may be a poloxamer (which are composed of a block of polyoxyethylene, followed by a block of polyoxypropylene, followed by a block of polyoxyethylene). The average number of units of polyoxyethylene and polyoxypropylene varies based on the number associated with the polymer. For example, the smallest polymer, poloxamer 101, consists of a block with an average of 2 units of polyoxyethylene, a block with an average of 16 units of polyoxypropylene, followed by a block with an average of 2 units of polyoxyethylene. Poloxamers range from colorless liquids and pastes to white solids. In cosmetics and personal care products, poloxamers are used in the formulation of skin cleansers, bath products, shampoos, hair conditioners, mouthwashes, eye makeup remover and other skin and hair products. Examples of poloxamers include, without limit, poloxamer 101, poloxamer 105, poloxamer 108, poloxamer 122, poloxamer 123, poloxamer 124, poloxamer 181, poloxamer 182, poloxamer 183, poloxamer 184, poloxamer 185, poloxamer 188, poloxamer 212, poloxamer 215, poloxamer 217, poloxamer 231, poloxamer 234, poloxamer 235, poloxamer 237, poloxamer 238, poloxamer 282, poloxamer 284, poloxamer 288, poloxamer 331, poloxamer 333, Poloxamer 334, poloxamer 335, poloxamer 338, poloxamer 401, poloxamer 402, poloxamer 403, poloxamer 407, poloxamer 105 benzoate, and poloxamer 182 dibenzoate.

In some particular embodiments, the surfactant is selected from a group consisting of TWEEN-20, TWEEN-80, ceteareth-20, SPAN-85, and combinations thereof. In one particular embodiment, the non-ionic surfactant is TWEEN-80.

In general, the amount of the surfactant in the total ointment formulation may range from about 0.1 to about 5.0 wt %. In various embodiments, amount of the surfactant in the total ointment formulation may range from about 0.1 to about 5.0 wt %, from about 0.4 to about 4.0 wt %, or from about 0.5 to about 1.0 wt %. In one particular embodiment, the amount of the surfactant in the total ointment formulation is about 0.5 wt %. In another particular embodiment, the amount of the surfactant in the total ointment formulation is about 0.8 wt %.

Lipid Material

The ointment formulation comprises a lipid material. The lipid material is used to equilibrate the lipid content of the wound, enhance the healing process of the wound, and acts as an emollient or moisturizer. A wide variety of lipid materials may be used in the ointment formulation, including a fatty acid, an oil, a wax, a triglyceride, or combinations thereof.

In one embodiment, the lipid material may be an oil. Non-limiting examples of an oil for use in the described formulations include mineral oil, squalene oil, flavor oils, silicon oil, essential oils, water insoluble vitamins, isopropyl stearate, butyl stearate, octyl palmitate, cetyl palmitate, tridecyl behenate, diisopropyl adipate, dioctyl sebacate, menthyl anthranhilate, cetyl octanoate, octyl salicylate, isopropyl myristate, neopentyl glycol dicarpate cetols, CERAPHYLS, decyl oleate, diisopropyl adipate, C12-C15 alkyl lactates, cetyl lactate, lauryl lactate, isostearyl neopentanoate, myristyl lactate, isocetyl stearoyl stearate, octyldodecyl stearoyl stearate, hydrocarbon oils, Isoparaffin, fluid paraffins, isododecane, petrolatum, argan oil, canola oil, chile oil, coconut oil, corn oil, cottonseed oil, flaxseed oil, grape seed oil, mustard oil, olive oil, palm oil, palm kernel oil, peanut oil, pine seed oil, poppy seed oil, pumpkin seed oil, rice bran oil, safflower oil, tea oil, truffle oil, vegetable oil, apricot (kernel) oil, jojoba oil (*Simmondsia chinensis* seed oil), grapeseed oil, macadamia oil, wheat germ oil, almond oil, rapeseed oil, gourd oil, soybean oil, sesame oil, hazelnut oil, maize oil, sunflower oil, hemp oil, bois oil, kuki nut oil, avocado oil, walnut oil, fish oil, berry oil, allspice oil, juniper oil, seed oil, almond seed oil, anise seed oil, celery seed oil, cumin seed oil, nutmeg seed oil, leaf oil, basil leaf oil, bay leaf oil, cinnamon leaf oil, common sage leaf oil, *eucalyptus* leaf oil, lemon grass leaf oil, *melaleuca* leaf oil, oregano leaf oil, patchouli leaf oil, peppermint leaf oil, pine needle oil, rosemary leaf oil, spearmint leaf oil, tea tree leaf oil, thyme leaf oil, wintergreen leaf oil, flower oil, chamomile oil, clary sage oil, clove oil, geranium flower oil, hyssop flower oil, jasmine flower oil, lavender flower oil, manuka flower oil, marhoram flower oil, orange flower oil, rose flower oil, ylang-ylang flower oil, bark oil, *cassia* bark oil, cinnamon bark oil, *sassafras* bark oil, wood oil, camphor wood oil, cedar wood oil, rosewood oil, sandalwood oil), rhizome (ginger) wood oil, resin oil, frankincense oil, myrrh oil, peel oil, bergamot peel oil, grapefruit peel oil, lemon peel oil, lime peel oil, orange peel oil, tangerine peel oil, root oil, valerian oil, oleic acid, linoleic acid, oleyl alcohol, isostearyl alcohol, semi-synthetic derivatives thereof, and any combinations thereof.

In particular embodiments, the lipid material is a moderate to long chain saturated or unsaturated fatty acid. Non-limiting examples of fatty acids include lauric acid, myristic acid, palmitic acid, stearic acid, arachidic acid, palmitoleic acid, oleic acid, linoleic acid, linolenic acid, or arachidonic acid.

The lipid material can be a plant based, animal based, or synthetic wax, including beeswax, cetyl palmitate, hydrogenated jojoba oil, microcrystalline wax, paraffin wax, carnuba wax, and rice bran wax.

The lipid material can be a triglyceride. Triglycerides are an ester derived from a glycerol and three fatty acids. In particular embodiments of the described ointments, the triglycerides are simple or mixed. Non-limiting examples of suitable triglycerides can be trilaurin, tristearin, triolein, caprylic/capric triglyceride, or combinations thereof.

In particular embodiments, the lipid material is selected from a group consisting of octyldodecanol, almond oil, isopropyl myristate, caprylic/capric triglycerides, and combinations thereof. In specific embodiments, the lipid material is caprylic/capric triglycerides.

The amount of the lipid material in the ointment formulation can and will vary depending on the other ingredients in the ointment. Generally, the amount of the lipid material in the total ointment formulation may range from about 0.05 to about 2.0 wt %. In various embodiments, the amount of the lipid material in the total ointment formulation may range from about 0.05 to about 2.0 wt %, from about 0.5 to about 1.5 wt %, or from about 0.6 to about 1.25 wt %. In one particular embodiment, the amount of the lipid material in the total ointment formulation may be about 1.25 wt %.

Terpene

The ointment formulation comprises at least one terpene. The terpene, as defined herein, is selected from a group consisting of a monoterpene, a diterpene, a triterpene, sesquiterpene, sesterterpenes, or combinations thereof. The terpene enhances the antibacterial, antimicrobial, and antifungal features of the ointment. Non-limiting examples of terpenes include myrcene, limonene, α-pinene, β-pinene, α-bisabolol, eucalyptol, trans-nerolidol, borneol, geraniol, cymene, eugenol, and combinations thereof. In some embodiments, the at least one terpene is selected from a group consisting of α-bisabolol, borneol, eugenol, or combinations thereof. In one preferred embodiment, the at least one terpene is α-bisabolol.

The amount of the terpene in the ointment formulation can and will vary depending on the formulation and the specific terpene. In general, the amount of the terpene in the total ointment formulation ranges from about 0.05 wt % to about 2.0 wt %. In various embodiments, the amount of the terpene in the total ointment formulation ranges from about 0.05 wt % to about 2.0 wt %, from about 0.5 to about 1.5 wt %, or from about 0.7 to 1.25 wt %. In one embodiment, the amount of the terpene in the total ointment formulation is about 1.0 wt %.

Nanoparticle

The ointment formulation includes a metal nanoparticle, and in particular embodiments, a metal oxide nanoparticle. In particular embodiments, the nanoparticle is in the context of a nanocomposite material. The nanoparticle provides antimicrobial, including antibacterial and antifungal properties to the ointment. These properties reduce and prevent wound infection and accelerates the wound healing. Non-limiting examples of these metal and metal oxide nanoparticles include zinc oxide, silver, gold, silver oxide, titanium oxide, copper oxide, magnesium oxide, or a combination of two or more of these nanoparticles. In various embodiments, the nanoparticle is copper oxide/zinc oxide nanoparticles, titanium oxide nanoparticles, silver nanoparticles, nanoparticles comprising magnesium oxide, or a combination of two or more nanoparticles. In certain embodiments, the nanoparticles comprise copper oxide/zinc oxide, or nanoparticles comprising magnesium oxide.

Additional examples of metal oxide nanocomposite materials (and their component nanoparticles), for use in the described ointment formulations can be produced according to methods described in U.S. Pat. Nos. 10,995,011 and 10,998,467, both of which are incorporated by reference herein in their entirety.

In a particular embodiment, the metal nanoparticle is in the context of a metal oxide nanocomposite. Briefly, the metal oxide nanocomposite for use in the described compositions is a semiconductor nanomaterial composition that includes metal oxide A and metal oxide B independently selected from a group comprising an alkaline earth metal, a d-block transition metal, f-block metal or combinations thereof; wherein the nanomaterial comprises clusters of metal oxide quantum dots, and wherein the hemostatic polymer is adhered or coated on the metal oxide semiconductor nanomaterial.

A wide variety of metal oxides may be used as metal oxide A and metal oxide B. In various embodiments the metal portion of metal oxide A and the metal portion of metal oxide B are independently selected from a group comprising an alkaline earth metal, a d-transition metal, f-transition, or combinations thereof. Non-limiting examples of suitable metal portion of alkaline earth metal oxides may be beryllium, magnesium, calcium, strontium, or barium. Non-limiting examples of the metal portion of suitable transition metal oxides may be scandium, titanium vanadium, chromium, manganese, iron, cobalt, nickel, copper, yttrium, zirconium, platinum, gold, mercury, niobium, iridium, molybdenum, technetium, ruthenium, rhodium, palladium, silver, cadmium, hafnium, tantalum, tungsten, rhenium, osmium, any lanthanide or zinc. In particular embodiments the metal portion of metal oxide A and the metal portion of metal oxide B are independently selected from a group consisting of titanium, manganese, nickel, silver, calcium, magnesium, zinc, copper, or combinations thereof.

In other particular embodiments, metal oxide A and metal oxide B are independently selected from a group consisting of zinc (ZnO), copper (CuO), or combinations thereof. The copper-zinc mixed oxide nanomaterial has a chemical formula of $CuO_{(1-x)}ZnO_x$, wherein x is the atomic ratio of the zinc oxide impurities on the nanomaterial. Generally, the value of x may range from about 0.01 to about 0.26. In various, the value of X may range from about 0.01 to about 0.26, or from about 0.03 to about 0.24. In a preferred embodiment, the value of x may be around 0.2. In other embodiments, in which a different nanocomposite is used, the doped impurities can be from 0.2 to 2.0.

Particular embodiments of the metal oxide nanocomposites for use in the described ointment formulation can be produced as follows. The process comprises: (a) providing a first aqueous solution comprising a soluble metal salt A and a soluble metal salt B; (b) providing a second aqueous solution comprising at least one soluble anion; (c) admixing the second aqueous solution with the first aqueous solution to form an insoluble precursor metal oxide semiconductor nanomaterial; (d) isolating the metal oxide semiconductor nanomaterial precursor; (e) drying the metal oxide semiconductor precursor; and (f) thermal decomposition of the metal oxide semiconductor precursor to form the metal oxide semiconductor nanomaterial.

(a) First Aqueous Solution

The process commences by preparing the first aqueous solution comprising a soluble metal salt A and a soluble metal salt B.

As appreciated by the skilled artisan, the soluble metal salts A and B are transformed into metal oxide A and metal oxide B after completion of the process.

A wide variety of soluble metal salts may be used in the process to prepare metal oxide A and metal oxide B. In various embodiments, soluble metal salt A and soluble metal salt B wherein the metal portion of these salts are independently selected from a group comprising an alkaline earth metal, a transition metal, or combinations thereof. Non-limiting examples of suitable metal portion of alkaline earth metal salts may be beryllium, magnesium, calcium, strontium, or barium. Non-limiting examples of the metal portion of suitable transition metal salts may be scandium, titanium vanadium, chromium, manganese, iron, cobalt, nickel, copper, yttrium, zirconium, platinum, gold, mercury, niobium, iridium, molybdenum, technetium, ruthenium, rhodium, palladium, silver, cadmium, hafnium, tantalum, tungsten, rhenium, osmium, any lanthanide, or zinc.

In preferred embodiments, soluble metal salt A and soluble metal salt B wherein the metal portion of these salts are independently selected from a group consisting of titanium, manganese, nickel, silver, calcium, magnesium, zinc, copper, or combinations thereof.

In particularly preferred embodiments, soluble metal salt A and soluble metal salt B wherein the metal portion of these salts are independently selected from a group consisting of zinc, copper, or combinations thereof.

A wide variety of anions may be used for soluble metal salt A and soluble metal salt B. An important aspect of these anions is that the anion is readily exchangeable, soluble in aqueous solution, non-toxic, pH neutral, and thermally decomposable. Non-limiting examples of suitable anions may be acetate, propionate, any soluble organic salt or combinations thereof. In a preferred embodiment, the anions used for soluble metal salt A and soluble metal salt B is acetate.

In other embodiments, the first aqueous solution may further comprise one or more different soluble salts than the soluble salts A and soluble salts B as described above.

The molar ratio of the soluble metal salt A to the soluble metal salt B may range from about 12:1 to about 1:12. In various embodiments, the molar ratio of the soluble metal salt A to the soluble metal salt B may range from about 12:1 to about 1:12, from about 11:1 to about 1:11, from about 10:1 to about 1:10, from about 9:1 to about 1:9, from about 8:1 to about 1:8, from about 7:1 to about 1:7, from about 7:1 to about 1:7, from about 6:1 to about 1:6, from about 5:1 to about 1:5, from about 4:1 to about 1:4, from about 3:1 to about 1:3, or from about 2:1 to about 1:2. In a preferred embodiment wherein soluble metal salt A is copper and the soluble metal salt B is zinc, the molar ratio may be about 2.3:1.

In general, the concentration of soluble metal salt A, soluble metal salt B, or combinations thereof in water may range from about 0.01M (moles/liter) to about 1.0M. In various embodiments, the concentration of the soluble metal salt A and soluble metal salt B may range from about 0.01M to about 1.0M, 0.03M to about 0.3M, or from 0.05M to 0.15M. In a preferred embodiment, the concentration of soluble metal salt A, soluble metal salt B, or combinations thereof in water may be about 0.15M.

The first aqueous solution may further comprise a stabilizer. Non-limiting examples of stabilizers may be a polyethylene glycol (PEG), polypropylene glycol (PPG), polyvinylpyrrolidone (PVP), polyvinylalcohol (PVA), Polyoxyethylene or combinations thereof. In a preferred embodiment, the stabilizer used in the first aqueous solution further comprises PEG, specifically PEG4000.

The concentration of the stabilizer in the first aqueous solution may range from about 0.0001M to about 0.001M. In various embodiments, the concentration of the stabilizer in the first aqueous solution may range from about 0.0001M to about 0.001M. In a preferred embodiment, the concentration of the stabilizer in the first aqueous solution may be preferably about 0.0007M.

The preparation of the first solution may be achieved by blending the soluble metal salt A, soluble metal salt B, water, an optional stabilizer, and an optional solvent in any known mixing equipment or reaction vessel until the mixture achieves homogeneity. These components may be added all at the same time, sequentially, or in any order.

In general, the preparation of the first aqueous solution may be conducted at a temperature that ranges from about 10° C. to about 40° C. In various embodiments, the temperature of the reaction may range from about 10° C. to about 40° C., from about 15° C. to about 35° C., or from about 20° C. to about 30° C. In one embodiment, the temperature of the reaction may be about room temperature (~23° C.). The reaction typically is performed under ambient pressure. The reaction may also be conducted under an inert atmosphere or air, for example under nitrogen, argon or helium.

The duration for preparing the first aqueous solution and will vary depending on many factors, such as the temperature, the method of mixing, and amount of materials being mixed. The duration of the reaction may range from about 5 minutes to about 12 hours. In some embodiments, the duration of the reaction may range from about 5 minutes to about 30 minutes, from about 30 minutes to about 2 hours, from about 2 hours to about 4 hours, from about 4 hours to about 10 hours, or from about 10 hours to about 12 hours. In various embodiments, the preparation may be allowed to continue until the first aqueous solution obtains homogeneity.

(b) Second Aqueous Solution

The second aqueous solution comprises at least one soluble anion source. An important aspect of these soluble anions is that anion is readily exchangeable, soluble in aqueous solution, is non-toxic, pH neutral, and thermally decomposable. Non-limiting examples of suitable anion sources may be lithium bicarbonate, sodium bicarbonate, potassium bicarbonate, and ammonium bicarbonate, or any alkaline oxalate, alkaline malate. In a preferred embodiment, the second aqueous solution comprises ammonium bicarbonate.

The second aqueous solution may be prepared by forming a reaction mixture comprising at least one soluble anion source, water, and optionally ethanol. These components may be added all at the same time, sequentially, or in any order. The second aqueous solution may be achieved by blending the above components in any known mixing equipment or reaction vessel until the mixture achieves a clear solution.

In general, the preparation of the second aqueous solution may be conducted at a temperature that ranges from about 10° C. to about 40° C. In various embodiments, the temperature of the preparation may range from about 10° C. to about 40° C., from about 15° C. to about 35° C., or from about 20° C. to about 30° C. In one embodiment, the temperature of the preparation may be about room temperature (~23° C.). The preparation typically is performed under ambient pressure. The preparation may also be conducted under air or an inert atmosphere, for example under nitrogen, argon or helium.

The duration for preparing the second aqueous solution and will vary depending on many factors, such as the temperature, the method of mixing, and amount of the at least one anion source being mixed. The duration of the reaction may range from about 5 minutes to about 12 hours. In some embodiments, the duration of the reaction may range from about 5 minutes to about 30 minutes, from about 30 minutes to about 2 hours, from about 2 hours to about 4 hours, from about 4 hours to about 10 hours, or from about 10 hours to about 12 hours.

Generally, the concentration of the at least one soluble anion source in the second aqueous solution may range from a concentration of about 0.10M to about 1.5M. In various embodiments, the concentration of the at least one soluble anion source in the second aqueous solution may range in a concentration from about 0.10M to about 1.5M, from about 0.2M to about 1.4M, or from about 0.3M to about 1.2M. In a preferred embodiment, the concentration of the at least one soluble anion source in the second aqueous solution may be about 0.3M.

(c) Preparation of the Insoluble Metal Oxide Semiconductor Nanomaterial Precursor.

The next step in the process is to prepare the insoluble metal oxide semiconductor nanomaterial precursor. Preparing the insoluble metal oxide semiconductor nanomaterial precursor occurs when the second aqueous solution comprising the at least one anion source is admixed with the first aqueous solution. As appreciated by the skilled artisan, once the second aqueous solution is admixed with the first aqueous solution, a chemical reaction occurs. In a preferred embodiment, the metal oxide semiconductor nanomaterial precursor comprising a copper zinc mixed carbonates are formed and can be depicted according to the following scheme.

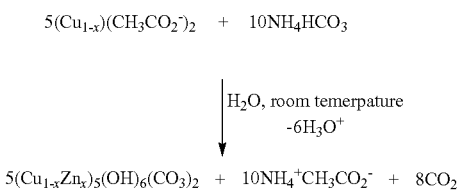

As appreciated by the skilled artisan, an advantage of using ammonium salt in the second aqueous solution is that by product, ammonium acetate, is water soluble, easily removed from the metal oxide semiconductor nanomaterial precursor, neutral pH at room temperature, and trace amount of ammonium acetate are readily thermally decomposed in the process.

The process may further comprise an organic solvent. The purpose of the solvent in the process is to reduce the foaming as the two aqueous solutions are combined, namely carbon dioxide. The addition of solvent may also cause a sudden change of the dielectric constant and change the dynamic of precipitation of the insoluble metal oxide semiconductor nanomaterial precursor. These changes may further lead to a hierarchic structure, a core-shell configuration of the metal oxide semiconductor nanomaterial, or combinations of both of properties. An additional property of the solvent is that solvent is volatile so excess amounts of solvent may be readily removed. Non-limiting examples of suitable solvents may be methanol, ethanol, propanol, iso-propanol, acetone or combinations thereof. In a preferred embodiment, the solvent in the process is ethanol.

Generally, the volume percent of the solvent in the mixture of the first aqueous solution, the second aqueous solution or combinations thereof may range from about 0.01 volume % to about 0.1 volume % In various embodiments, the volume percent of the solvent in the mixture of the first aqueous solution, the second aqueous solution or combinations thereof may range from about 0.01 volume % to about 0.1 volume %, from about 0.02 volume % to about 0.08 volume %, or from about 0.03 volume % to about 0.07 volume %. In a preferred embodiment, the volume percent of the solvent in the mixture of the first aqueous solution, the second aqueous solution or combinations thereof may be about 0.02 volume %.

The solvent may be added to the first aqueous solution, the second aqueous solution, or the combination of the first aqueous solvent and the second aqueous solvent, or combinations thereof.

The metal oxide semiconductor nanomaterial precursor may be prepared by forming a reaction mixture comprising the first aqueous solution, the second aqueous solution, and the optional solvent. The metal oxide semiconductor nanomaterial precursor may be achieved by blending the above components in any known mixing equipment or reaction vessel or static mixer until the mixture achieves completeness of reaction.

In an embodiment, the second aqueous solution may be added to the first solution. Generally, the second aqueous solution is added immediately in a batch o by a static mixer continuously in a range from about 20 volume % to about 45 volume % to the first aqueous solution. In a speed from 1 to 10 l/min, in various embodiments from 1.25 to 8 l/min. In a preferred embodiment 5 to 6 l/min. This quick addition ensures the chemical reaction depicted above goes to completion.

Since the insoluble metal oxide semiconductor nanomaterial precursor precipitates from an aqueous solution, the method of stirring to prepare the precursor is important so amounts of the soluble metal salt A, metal salt B, or the at least one soluble anion source does not become entrained in the insoluble metal oxide semiconductor nanomaterial precursor. Generally, the process may be stirred mechanically at a speed from about 250 rpm (revolution per minute) to about 1000 rpm. In various embodiments, the stirring speed may range from 250 rpm to about 1200 rpm, from about 300 rpm to about 1000 rpm, or from about 500 rpm to about 900 rpm. In a preferred embodiment, the stirring speed of the process may be about 700 rpm.

In general, the preparation of the insoluble metal oxide semiconductor nanomaterial precursor may be conducted at a temperature that ranges from about 10° C. to about 65° C. In various embodiments, the temperature of the preparation may range from about 10° C. to about 65° C., from about 15° C. to about 35° C., or from about 20° C. to about 30° C. In one embodiment, the temperature of the preparation may be about room temperature (~23° C.). The preparation typically is performed under ambient pressure. The preparation may also be conducted under air or an inert atmosphere, for example under nitrogen, argon or helium.

The pH during the addition of the reaction between the second aqueous solution and the first aqueous solution may range from about 6.0 to about 8.0. In various embodiments, the pH of the process may range from about 6.0 to about 8.0, from about 6.5 to about 7.5, or from about 6.7 to about 7.3. In a preferred embodiment, the pH of the process is about 6.8 to 7.0.

The duration for preparing the insoluble metal oxide semiconductor nanomaterial precursor and will vary depending on many factors, such as the temperature, the method of mixing, and scale of the process. The duration of the reaction may range from about 5 minutes to about 6 hours. In some embodiments, the duration of the reaction may range from about 5 minutes to about 6 hours, from about 15 minutes to about 4 hours, or from about 20 minutes to about 1 hour. In a preferred embodiment, the duration for preparing the insoluble metal oxide semiconductor precursor may be about 30 minutes.

(d) Isolating the Insoluble Metal Oxide Semiconductor Nanomaterial Precursor

The next step in the process is isolating the insoluble metal oxide semiconductor nanomaterial precursor from the reaction mixture in step (c) comprising water, the stabilizer, and the optional solvent. As appreciated by the skilled artisan, there are many methods of isolating the insoluble metal oxide semiconductor nanomaterial precursor from the reaction mixture in step (c). Non-limiting methods may be filtration, centrifugal separation, decantation, or combinations thereof. The insoluble metal oxide semiconductor nanomaterial precursor, after isolation, may be rinsed with water, ethanol, or combinations thereof. The precursor is washed with water, ethanol, or combinations thereof solvent until the supernatant is colorless or the precursor color remains constant.

(e) Drying the Insoluble Metal Oxide Semiconductor Precursor.

The next step in the process is drying the insoluble metal oxide semiconductor nanomaterial precursor from the reaction mixture in step (d). This step would remove excess amounts of solvent from the insoluble metal oxide semiconductor nanomaterial precursor. As appreciated by the skilled artisan, many devices are available to dry the precursor. Non-limiting examples for drying the solid may be batch driers, convection ovens, rotary dryers, drum dryers, kiln dryers, flash dryers, or tunnel dryers.

In general, the drying of the insoluble metal oxide semiconductor nanomaterial precursor may be conducted at a temperature that ranges from about 30° C. to about 120° C. In various embodiments, the temperature of the preparation may range from about 30° C. to about 120° C., from about 40° C. to about 100° C., or from about 50° C. to about 80° C. In one embodiment, the temperature of drying may be about 60° C. The preparation typically is performed under ambient pressure. The preparation may also be conducted under air or an inert atmosphere, for example under nitrogen, argon or helium.

The duration for drying the insoluble metal oxide semiconductor nanomaterial precursor and will vary depending on many factors, such as the temperature, the amount of the precursor, and type of the dryer. The duration of the reaction may range from about 30 minutes to about 48 hours. In some embodiments, the duration of the reaction may range from about 30 minutes to about 48 hours, from about 1 hour to about 24 hours, or from about 2 hours to about 4 hours. In a preferred embodiment, the duration for drying the insoluble metal oxide semiconductor precursor may be about 3 hours, or until the drying the insoluble metal oxide semiconductor precursor reaches less than 12% moisture.

(f) Thermal Decomposition of the Insoluble Metal Oxide Semiconductor Nanomaterial Precursor Forming the Metal Oxide Semiconductor Nanomaterial The next step in the process is thermal decomposition of the insoluble metal oxide semiconductor nanomaterial precursor forming the metal oxide semiconductor nanomaterial. This step removes transforms the thermally labile ligand forming the oxides and removes by-products and impurities that were not removed in step (d). As appreciated by the skilled artisan, carbon, hydrogen and excessive oxygen may be released in forms of carbon dioxide and water steam from the thermally labile ligands, by-products, and impurities. In a preferred embodiment, the metal oxide semiconductor nanomaterial precursor comprising a copper zinc mixed oxide is thermally decomposed to form the metal oxide semiconductor nanomaterial. This reaction can be depicted according to the following scheme.

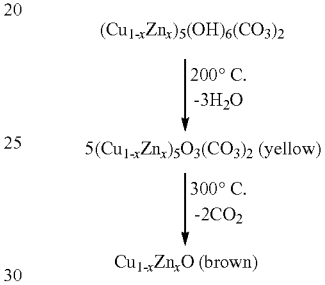

In general, thermal decomposition of the insoluble metal oxide semiconductor nanomaterial precursor may be conducted at a temperature that ranges from about 200° C. to about 1000° C. In various embodiments, the temperature of the preparation may range from about 200° C. to about 1000° C., from about 225° C. to about 800° C., or from about 250° C. to about 350° C. In one embodiment, the temperature of drying may be about 300° C. The preparation typically is performed under ambient pressure. The preparation may also be conducted under air or an inert atmosphere, for example under nitrogen, argon or helium.

The duration for drying the insoluble metal oxide semiconductor nanomaterial precursor and will vary depending on many factors, such as the temperature, the amount of the precursor, and type of the dryer. The duration of the reaction may range from about 5 minutes to about 48 hours. In some embodiments, the duration of the reaction may range from about 10 minutes to about 48 hours, from about 15 hour to about 24 hours, or from about 2 hours to about 4 hours. In a preferred embodiment, the duration for drying the insoluble metal oxide semiconductor precursor may be about 0.3 hour.

The yield of the metal oxide semiconductor material from the process described above may range from 5 to 12 g/L. with high purity.

The amount of the nanoparticle in the ointment formulation can and will vary depending on the nanoparticle and other components of the ointment. Generally, the amount of the nanoparticle in the total ointment formulation ranges from about 0.05 wt % to about 2.0 wt %. In various embodiments, the amount of the nanoparticle in the total ointment formulation ranges from about 0.05 wt % to about 2.0 wt %, from about 0.1 to 1.0 wt %, or from about 0.2 to about 0.5 wt %. In one preferred embodiment, the amount of the nanoparticle in the total ointment formulation may be about 0.2 wt %. In another preferred embodiment, the amount of the nanoparticle in the total ointment formulation may be about 0.5 wt %.

In a particular embodiment, the nanoparticle/nanocomposite is provided in the ointment formulation as a pre-mixed suspension with PEG. In a particular embodiments in which the formulation is composed of multiple PEGs, the nanoparticle is pre-mixed with a portion, such as 50%, 40%, 30%, 25%, 20% 15%, 10% or less of the low or lower molecular weight PEG. For example, in particular embodiments, the ointment includes a mixture of PEG-400 and PEG-4000, and the nanoparticle is first combined with a portion, such as 25% of the total amount, of the PEG-400, prior to its combination with the other ointment components.

Glycerin

In particular embodiments, the described ointment formulation further includes glycerin. The inclusion of glycerin in the ointment formulation enhances water retention of the wound, and together with other components of the ointment enhances the rate of wound healing. The amount of glycerin in the total ointment formulation can range from about 0 to about 5.0 wt %, such as from about 1.0-4.0 wt %, or from about 2.0-3.0 wt %.

III. Methods for Preparing the Ointment Formulation

Also described herein are methods for preparing the described ointment formulation. The method includes combining the mixture of polyethylene glycols at an elevated temperature (when more than one PEG is in the composition); contacting the polyethylene glycols with the surfactant, the lipid material, the at least one terpene, and glycerin forming a mixture; and contacting the mixture with a suspension of the nanoparticle in the polyethylene glycol at the elevated temperature; and cooling the mixture to room temperature to form the ointment formulation. This process can be conducted in a batch mode or a semi-continuous mode.

Contacting the Mixture of Polyethylene Glycols

As described herein, particular embodiments of the described ointment formulations include more than one PEG, such as two, three, four or more PEGs of different molecular weight. In such embodiments, one step in the method for producing the described ointment includes contacting (mixing) the two polyethylene glycols at elevated temperature to form a mixture of polyethylene glycols. The specific PEGs are described in more detail above. In such embodiments where there are at least two PEGs, the PEG mixture includes one of lower molecular weight and one of higher molecular weight.

In general, the weight ratio of the lower molecular weight PEG to the higher molecular weight PEG ranges from about 2.0:1.0 to about 5.0:1.0. In various embodiments, the weight ratio of the lower molecular weight PEG to the higher molecular weight PEG ranges from about 2.0:1.0 to about 5.0:1.0, from about 2.5:1.0 to about 4.0:1.0, or from about 2.85:1.0 to about 3.85:1.0.

In general, the PEGs are combined at a temperature that ranges from about 20° C. to about 100° C., such as from about 25° C. to about 100° C., from about 40° C. to about 90° C., or from about 60° C. to about 70° C. The temperature at which the PEGs are combined will depend in part on the PEGs to be combined. For example, PEG of greater molecular weight will require higher temperature to be combined than PEG of lower molecular weight. In one embodiment, the PEGs are combined from about 65° C. to about 70° C. The mixing typically is performed under ambient pressure. The mixing may also be conducted under an inert atmosphere, for example under nitrogen, argon or helium. The duration of the mixing may range from about 5 minutes to about 1 hour. In some embodiments, the duration of the mixing may range from about 5 minutes to about 30 minutes, from about 30 minutes to about 45 minutes, or from about 45 minutes to about 1 hour. In one particular embodiment, the mixing may be allowed to proceed for about 1 hour. This temperature provides a homogenous and transparent base for the ointment formulation.

Contacting the Polyethylene Glycol(s) with the Surfactant, the Lipid Material, the at Least One Terpene, and Glycerin Forming a Mixture The surfactant, lipid material, at least one terpene, and glycerin (if present) are mixed with the PEG or PEGs, after the PEGs have been combined. The surfactant, lipid material, at least one terpene, and optional glycerin can be added in any order and either separately or in combination, or sub-combinations, thereby forming a mixture with the PEGs. The noted components can be combined at a temperature that ranges from about 20° C. to about 100° C., such as from about 25° C. to about 100° C., from about 40° C. to about 90° C., or from about 60° C. to about 70° C. In one embodiment, the components can be combined at temperature that ranges from about 65° C. to about 70° C. The mixing typically is performed under ambient pressure. The mixing may also be conducted under an inert atmosphere, for example under nitrogen, argon or helium.

The duration of the mixing may range from about 5 minutes to about 1 hour, such as from about 5 minutes to about 30 minutes, from about 30 minutes to about 45 minutes, or from about 45 minutes to about 1 hour. In a particular embodiment, the composition is mixed for about 1 hour.

Contacting the Mixture with a Suspension of the Nanoparticle in the Polyethylene Glycol at the Elevated Temperature The metal or metal oxide nanoparticle/nanocomposite can, in certain embodiments, be combined with part, (¼ to ⅓), of the PEG with lower molecular weight as a pre-mixed suspension of the nanoparticle in polyethylene glycol (NP-PEG). In particular embodiments, the NP-PEG suspension is added to the mixture of PEG or mixed PEG combination with the surfactant, lipid material, at least one terpene, and optional glycerin. In other embodiments the NP-PEG suspension is added after the surfactant, lipid material, at least one terpene, and optional glycerin are combined with the PEG or mixed PEG combination. The suspension of the nanoparticle in polyethylene glycol can be added portion wise or all at once.

In general, the weight % of the nanoparticle in the polyethylene glycol ranges from 1.0:10.0 to about 1.0:200.0. In various embodiments, the weight percent of the nanoparticle in the polyethylene glycol ranges from 1.0:10.0 to about 1.0:200.0, from about 1.0:25.0 to about 1.0:150.0, or from about 1.0:40.0 to about 1.0:100.0. In one preferred embodiment, the weight percent of the nanoparticle in the polyethylene glycol may be about 1.0:40.0. In another preferred embodiment, the weight percent of the nanoparticle in the polyethylene glycol may be about 1.0:100.0.

The nanoparticle-PEG (NP-PEG) combination can be added to the other ointment components at a temperature that ranges from about 20° C. to about 100° C., such as from about 25° C. to about 100° C., from about 40° C. to about 90° C., or from about 60° C. to about 70° C. In one embodiment, the components can be combined at temperature that ranges from about 65° C. to about 70° C. The mixing typically is performed under ambient pressure. The mixing may also be conducted under an inert atmosphere, for example under nitrogen, argon or helium. The duration of mixing after the addition of the nanoparticle-PEG combination can range from about 5 minutes to about 1 hour, such as from about 5 minutes to about 30 minutes, from about 30 minutes to about 45 minutes, or from about 45 minutes to about 1 hour. In a particular embodiment, the duration of mixing is about 1 hour.

Cooling the Mixture to Room Temperature to Form the Ointment Formulation

After all of the components of the described ointment formulation are combined in a homogenous mixture, the warm ointment formulation is cooled to room temperature with continuous mixing. This cooling process allows the ointment to maintain homogeneity of the ointment. The time of cooling of the ointment formulation, can and will vary depending on the batch size of the ointment. Generally, the time in the cooling process may range from 1 hour to about 48 hours. In various embodiments, the time in the cooling process may range from 1 hour to about 48 hours, from about 12 hours to about 36 hours, or from 18 hours to about 24 hours.

IV. Methods of Using the Ointment Formulation

Provided herein is an antimicrobial ointment formulation for use in methods of wound treatment, such as general wound treatment and/or treating and/or preventing infection in or on a wound. The described ointment formulations possess antimicrobial, such as antibacterial and antifungal properties, and as well as analgesic, antioxidant, anti-inflammatory properties, skin moisturizing, and emollient properties.

In particular embodiments, the described ointment formulation can be applied (i.e. contacted) directly to a wound. In other embodiments, the ointment formulations can be applied onto a wound dressing, such as a bandage, which is then applied (i.e. contacted) to a wound.

The methods of treatment described herein include administering to a subject in need thereof an effective amount, such as a therapeutically effective amount, of the described antimicrobial anhydrous topical ointment, thereby treating the wound. In particular embodiments the antimicrobial anhydrous topical ointment without other additives. In other embodiments, the antimicrobial anhydrous topical ointment is included in a pharmaceutical composition that includes pharmaceutically acceptable carriers, salts, excipients and the like. In still other embodiments, the ointment is further combined with other active ingredients such as analgesic and anti-inflammatory drugs known to the art.

In particular embodiments, the wound is an acute wound. In other embodiments, the wound is a chronic wound. The wound for treatment with the described ointment can be an open wound (i.e. the skin is broken) or a closed wound or burn. In certain embodiments, the described ointment is re-administered (e.g. re-applied) to the wound, either directly or in the process of changing a wound dressing. In certain embodiments the subject is a human subject; in other embodiments, the subject is a non-human animal.

The described methods of treatment inhibit and/or prevent microbial growth on and in the wound under treatment. Examples of microbes and microbial infections that can be inhibited and/or prevented include bacteria (Gram positive and negative) and fungi. Particular examples of bacteria that can be inhibited and/or prevented by contact with the described ointment formulation include, but are not limited to, species of *Staphylococcus*, such as *Staphylococcus aureus*, *Staphylococcus epidermidis*, and the like; *Enterococcus*, such as *Enterococcus faecalis*, *Enterococcus faecium*, and the like; *Salmonella*, such as *Salmonella typhi*, *Salmonella typhimurium*, *Salmonella enterica*, and the like; *Escherichia*, such as *Escherichia coli*, and the like; *Streptococcus*, such as *Streptococcus pneumoniae*, *Streptococcus pyogenes*, *Streptococcus agalactiae*, and the like; *Helicobacter*, such as *Helicobacter pylori*, and the like; *Campylobacter*, such as *Campylobacter jejuni*, and the like; as well as the species of genera *Yersinia*, *Chlamydia*, *Coxilla*, *Cutibacterium*, *Ehrlichia*, *Francisella*, *Legionella*, *Pasteurella*, *Brucella*, *Proteus*, *Klebsiella*, *Enterobacter*, *Tropheryma*, *Acinetobacter*, *Aeromonas*, *Alcaligenes*, *Capnocytophaga*, *Bacillus*, *Clostridium*, *Corynebacterium*, *Erysipelothrix*, *Listeria*, *Pseudomonas*, and the like. Examples of infections that can also be treated with the described ointment formulation include infections caused by fungi such as *Candida albicans*, *Microsporum canis*, *Sporothrix schenckii*, *Trichophyton rubrum*, *Trichophyton mentagrophytes*, *Malassezia furfur*, *Pityriasis versicolor*, *Exophiala werneckii*, *Trichosporon beigelii*, *Coccidioides immitis*, *Blastomyces dermatitidis*, *Aspergillus fumigatus*, *Epidermophyton* spp., *Fusarium* spp., Zygomyces spp., *Rhizopus* spp. *Mucor* spp., and so forth.

Furthermore, the described ointment formulations can be applied for inhibiting or preventing the growth of microorganisms that are resistant to at least one antimicrobial agent. It will be appreciated that the drug-resistant microorganisms that can be inhibited by the described formulations include microorganisms that are resistant in view of a biological resistance (e.g. expression of a drug resistance gene) or environmental resistance, (e.g. as a result of a higher order microbial community such as a biofilm). The term "antimicrobial agent" used herein refers to any naturally or synthetically derived agent that kills microorganisms or inhibits the growth thereof, directly, or indirectly, and includes conventional antibiotics as well as synthetic chemotherapeutic agents, such as sulfonamides, isoniazid, ethambutol, AZT, synthetic peptide antibiotics, and the like.

Thus, in a specific embodiment, the microbes inhibited or prevented by the described ointment formulation include antimicrobial-resistant strains of microorganisms mentioned above, in particular, of *Staphylococcus aureus*, *Enterococcus faecium*, *Enterococcus faecalis*, *E. coli*, *Salmonella typhi*, *Campylobacter jejuni*, *Klebsiella pneumoniae*, *Neisseria gonorrhoeae*, *Candida albicans*, *Pseudomonas* spp., and the like.

More specifically, such antimicrobial-resistant organisms include methicillin-resistant *Staphylococcus aureus* (MRSA), vancomycin-resistant enterococci (VRE), ampicillin-resistant *E. coli* (e.g., *E. coli* O157:H7), fluoroquinolone-resistant *Salmonella thyphi*, ceftazidime-resistant *Klebsiella pneumoniae*, fluoroquinolone-resistant *Neisseria gonorrhoeae*, and the like.

The following examples are provided to illustrate certain particular features and/or embodiments. These examples should not be construed to limit the disclosure to the particular features or embodiments described.

EXAMPLES

Example 1: Antimicrobial Effect of Metal Oxide Nanoparticles

The antimicrobial effect of an illustrative metal oxide nanocomposite was determined according to the ASTM International standard assessment of antimicrobial activity using a time-kill procedure. (available online at astm.org/cgi-bin/resolver.cgi?E2315-16).

Briefly, after 2 h of preconditioning using 5% FBS, 0.5 ml bacterial suspension ($2\times10^8$) was mixed into the noted amount of the nanocomposite and the test tube was incubated at 30° C. for 2 h. At the end of incubation, a sample was taken and serially diluted and plated.

The nanocomposite additive is composed of primary nanocrystallites of $Zn^{+2}$ ion doped CuO (~15 nm) phase and pure ZnO (~10 nm) phase.

As shown in FIG. 1, media containing 0.2% of the $CuO_{(1-x)}ZnO_x$ nanocomposite nearly eradicates *S. aureus* in the solution. A greater than 5-fold log reduction in growth was observed, which was equal to approximately 99.9% reduction in comparison to control.

Example 2: Poor Antimicrobial Activity of Standard Ointment Formulations

Example 1 illustrates that the $CuO_{(1-x)}ZnO_x$ nanocomposite is a robust antimicrobial compound. In other experiments, this nanocomposite exhibited strong broad-spectrum antibacterial activity, both in suspension and when in medical gauze and acrylic paints, against *Escherichia coli*, *Listeria monocytogenes*, Methicillin-resistant *Staphylococcus aureus* and *Salmonella enterica* Serovar Typhimurium. To develop an effective topical application for treatment of an open wound or burn, different non-occlusive vehicles were initially screened to produce a semi-solid ointment formulation incorporating the antimicrobial nanocomposite. As shown below, none of tested formulations tested demonstrated a strong antimicrobial effect.

Formulation 1: Anionic Cream Using 0.2% of $CuO_{(1-x)}ZnO_x$

| Ingredients | % w/w | Mass (g) per 200 g |
|---|---|---|
| Water phase | | |
| Propylene glycol | 2 | 4 |
| Glycerin | 2 | 4 |
| Water | 78.7 | s.a.f.* |
| Oil phase | | |
| Isopropyl myristate | 7 | 14 |
| Cetyl alcohol | 8 | 16 |
| Emulsifier | | |
| Sodium dodecyl sulfate | 1 | 2 |
| Active additives | | |
| $CuO_{(1-x)}ZnO_x$ | 0.2 | 0.4 |
| Bisabolol | 1 | 2 |

*Sufficient amount for

Preparation

¾th the total volume of water was heated at 70° C. To this was added the emulsifier and bisabolol. The components of the oil phase were heated separately at 65° C. After both the phases reached targeted temperature, the oil phase was slowly poured into the water phase under continuous stirring. The suspension of $CuO_{(1-x)}ZnO_x$ nanocomposite was prepared in the remaining ¼th volume of water under sonication and the temperature raised to 70° C. 5 minutes after mixing oil and water phase, the suspension of nanocomposite was added to the mixture and cooled down under stirring until the temperature reached 30° C.

Antibacterial Activity

The formulation was tested by ASTM E2315-16 standard against *Staphylococcus aureus* with and without 2 hour conditioning with 5% FBS. No antibacterial activity was detected after 2 hour of contact time.

Formulation 2: Non-Ionic Cream Using 0.2% of $CuO_{(1-x)}ZnO_x$

| Ingredient | % w/w | Mass (g) per 200 g |
|---|---|---|
| Water phase | | |
| Propylene glycol | 2 | 4 |
| Glycerin | 2 | 4 |
| Water | 74.4 | s.a.f.* |
| Oil phase | | |
| Isopropyl myristate | 4 | 8 |
| Cetyl alcohol | 6 | 12 |
| Caprylic/capric triglycerides | 8 | 16 |
| Emulsifier | | |
| Ceteareth-20 | 2 | 4 |
| Span 80 | 0.4 | 0.8 |
| Active additives | | |
| $CuO_{(1-x)}ZnO_x$ | 0.2 | 0.4 |
| Bisabolol | 1 | 2 |

*Sufficient amount for

Preparation

¾th the total volume of water was heated at 70° C. and the Ceteareth-20 and Bisabolol was added to it. The components of oil phase and Span 80 were heated separately at 65° C. After both phases reached the targeted temperature, the oil phase was slowly poured into the water phase under continuous stirring. The suspension of $CuO_{(1-x)}ZnO_x$ nanocomposite was heated in the remaining ¼th the volume of water under sonication and the temperature raised to 70° C. 5 minutes after mixing oil and water phase, the suspension of nanocomposite was added to the mixture and cooled down under stirring until the temperature reached 30° C.

Antibacterial Activity

The formulation was tested by ASTM E2315-16 standard against *Staphylococcus aureus* with and without 2 h conditioning with 5% FBS. After 2 h of contact time, there was low antibacterial activity of 1 log reduction without any conditioning. No antibacterial activity was observed with conditioning.

Formulation 3: Stearic Vanishing-Cream Including 0.2% of $CuO_{(1-x)}ZnO_x$

| Ingredient | % w/w | Mass (g) per 200 g |
|---|---|---|
| Water phase | | |
| Propylene glycol | 3 | 6 |
| Tri-ethanol amine 20% w/v | 1.3 | 2.6 |
| Water | 72.5 | s.a.f.* |
| Oil phase | | |
| Isopropyl myristate | 4 | 8 |
| Glyceryl stearate | 5 | 10 |
| Emulsifier | | |
| Tween 20 | 7 | 14 |
| Stearic acid | 6 | 12 |
| Active additives | | |
| $CuO_{(1-x)}ZnO_x$ | 0.2 | 0.4 |
| Bisabolol | 1 | 2 |

*Sufficient amount for

Preparation:

¾th the total volume of water was heated at 70° C. and to it was added TWEEN-20 surfactant and Bisabolol. The components of the oil phase and stearic acid were heated separately at 65° C. After both phases reached the targeted temperature, the oil phase was slowly poured into the water phase under continuous stirring. The suspension of $CuO_{(1-x)}ZnO_x$ nanocomposite was prepared in the remaining ¼th of the volume of water under sonication and the temperature raised to 70° C. 5 minutes after mixing oil and water phase, the suspension of nanocomposite was added to the mixture and cooled down under stirring until the temperature reached 30° C.

Antibacterial Activity

The formulation was tested by ASTM E2315-16 standard against *Staphylococcus aureus* with and without 2 h conditioning with 5% FBS. No antibacterial activity was detected after 2 h of contact time.

Example 3: Preparation of Antimicrobial Ointment Formulations

Example 2 showed that several screened ointment types, including an anionic o/w emulsion based on Novo-Base II, a non-ionic neutral o/w emulsion, and a fat reduced emulsion in gel, showed no antimicrobial activity, despite including an antimicrobial nanocomposite. This and the following example show that in contrast, the ointment formulation described herein has robust antimicrobial activity.

The active ingredients in the tested formulation were $CuO_{(1-x)}ZnO_x$ nanocomposite (0.2%) and α-bisabolol (1%). As shown in Example 1, $CuO_{(1-x)}ZnO_x$ provides a broad spectrum of robust antimicrobial protection. α-bisabolol possesses antioxidant, anti-inflammatory, antimicrobial and regenerative properties. Other ingredients including polyethylene glycol (PEG), TWEEN 80 (non-ionic surfactant), capric triglyceride (lipid material), and glycerin were added to enhance other physical properties such as hydrophilicity, spreadability, stability and homogeneity, moisturizing, and water retention at the wound bed.

A particular embodiment of the developed formulation was produced as follows. Into a 2-L round bottom flask equipped with a heating mantle was added 570 g of PEG400 and 220 g of PEG 4000. This mixture was heated to 67±3° C., under continuous gentle mixing. To the mixture of the PEGs was added 10 g caprylic/capric triglycerides, 8 g TWEEN-80 surfactant, and 10 g α-bisabolol. This mixture was stirred at 67±3° C. for 30 minutes to 1 hour. At that time, a suspension of 2 g $CuO_{1-x}/ZnO_x$ nanocomposite in 200 g PEG400 was added in portions. This mixture was stirred at 67±3° C. for 60 min to ensure homogeneous mixing. The ointment formulation was cooled to 30° C. under continuous mixing and then to room temperature.

Another exemplary ointment formulation was prepared as follows. Into a 2-L round bottom equipped with a heating mantle was added 570 g of PEG400 and 220 g of PEG 4000. This mixture was heated to 67±3° C., under continuous gentle mixing. To the mixture of the PEGS was added 10 g caprylic/capric triglycerides, 8 g TWEEN-80 surfactant, and 10 g α-bisabolol. This mixture was stirred at 67±3° C. for 30 minutes to 1 hour. At that time, a suspension of 5 g $CuO_{1-x}/ZnO_x$ nanocomposite in 200 g PEG400 was added in portions. This mixture was stirred at 67±3° C. for 60 min to ensure homogeneous mixing. The ointment formulation was cooled to 30° C. under continuous mixing and then to room temperature.

In a third exemplary embodiment, the ointment formulation was produced in two steps. In the first step, 1% $CuO_{(1-x)}ZnO_x$ suspension was prepared in PEG-400 using a homogenizer. In the second step, PEG-400 (572 g) and PEG-4000 (200 g) were mixed at 70° C. To this was added capric triglyceride (8 g), TWEEN 80 surfactant (8 g), and α-bisabolol (10 g) while continuously mixing at 70° C. for 30 min. Finally, 1% $CuO_{(1-x)}ZnO_x$ in PEG-400 (200 g) was added and mixed for additional 60 min. Brown semi-solid formulation was obtained after slowly cooling above mixture. Antimicrobial activity of the formulation was evaluated against several microbial species relevant to wound management (Table 1) as follows.

Ointment was tested according to ASTM E2315, a standard guide for assessment of antimicrobial activity using a time-kill procedure. After 2 h of preconditioning using 5% FBS to simulate effect of wound exudates on ointment activity, 0.5 ml bacterial suspension ($2\times10^8$) was mixed into 10 g ointment and the test tube was incubated at 30° C. for 2 h. At the end of incubation, 1 g sample was taken and serially diluted and plated. As shown in Table 1, the ointment formulation was found highly effective against tested against *E. coli, P. Aeruginosa*, MRSA, *C. acne, C. Albicans*, and *A. niger*. For all species tested, the anti-microbial effect was ≥99.66%.

TABLE 1

| Antimicrobial efficacy of ointment formulation | | |
|---|---|---|
| | Microbial species | Average log reduction |
| Gram negative | E. coli | 5.9 |
| | P. Aeruginosa | 6.3 |
| Gram positive | MRSA | 6.4 |
| | C. acne | 2.935 |
| Fungi | C. albicans | 4.8 |
| | A. niger | 2.472 |

Example 4: Additional Antimicrobial Ointment Formulations

Example 3 demonstrated the antimicrobial efficacy of the ointment formulation described herein. This example compares and demonstrates similar efficacy with ointments containing different metal nanoparticles/nanocomposites.

Non-Greasy Ointment Using PEG Polymers and 0.2% of $CuO_{(1-x)}ZnO_x$

| Ingredient | % w/w | Mass (g) per 200 g |
|---|---|---|
| Hydrophilic phase | | |
| PEG 4000 | 20 | 40 |
| PEG 400 | 75.4 | 150.8 |
| Propylene glycol | 1 | 2 |
| Oil phase | | |
| Isopropyl myristate | 1 | 2 |
| Caprylic/capric triglycerides | 1 | 2 |
| Emulsifier | | |
| TWEEN 80 | 0.4 | 0.8 |
| Active additives | | |
| $CuO_{(1-x)}ZnO_x$ | 0.2 | 0.4 |
| Bisabolol | 1 | 2 |

Preparation

The hydrophilic phase was heated to 75° C. using ¾th the total volume PEG 400. The components of oil phase and Bisabolol were separately heated at 65° C. After both phases reached targeted temperature, the oil phase was slowly poured into the hydrophilic phase under continuous stirring.

The suspension of $CuO_{(1-x)}ZnO_x$ nanocomposite was compared in the remaining ¼th the volume of PEG 400 using high speed homogenizer at 20000 rpm and kept at 70° C. 15 minutes after mixing oil and hydrophilic phase, the suspension of nanocomposite was added to the mixture and cooled under stirring until the temperature reached 30° C.

Antibacterial Activity

The 0.2% $CuO_{(1-x)}ZnO_x$ formulation was tested by ASTM E2315-16 standard against *Staphylococcus aureus* with and without 2 h conditioning with 5% FBS. After 2 h of contact time, high antibacterial activity of 4 log reduction was observed under both conditions.

Non-Greasy Ointment Using PEGs and 0.5% Magnesium Oxide (MgO) Nanoparticles

| Ingredient | % w/w | Mass (g) per 200 g |
|---|---|---|
| Water phase | | |
| PEG 4000 | 20 | 40 |
| PEG 400 | 75.1 | 150.2 |
| Propylene glycol | 1 | 2 |
| Oil phase | | |
| Isopropyl myristate | 1 | 2 |
| Caprylic/capric triglycerides Emulsifier | 1 | 2 |
| TWEEN 80 | 0.4 | 0.8 |
| Active additives | | |
| MgO | 0.5 | 1 |
| Bisabolol | 1 | 2 |

This formulation was prepared as described above for the 0.2% $CuO_{(1-x)}ZnO_x$ formulation. Antimicrobial activity was similarly tested by the ASTM E2315-16 standard against *Staphylococcus aureus*. After 2 h of contact time, high antibacterial activity of 3 log reduction was observed under both conditions tested (with and without preconditioning).

Non-Greasy Ointment of PEGs and 1% ZnO Nanoparticles

| Ingredient | % w/w | Mass (g) per 200 g |
|---|---|---|
| Water phase | | |
| PEG 4000 | 19 | 38 |
| PEG 400 | 75.4 | 150.8 |
| Propylene glycol | 1 | 2 |
| Oil phase | | |
| Isopropyl myristate | 1 | 2 |
| Caprylic/capric triglycerides Emulsifier | 1 | 2 |
| TWEEN 80 | 0.4 | 0.8 |
| Active | | |
| ZnO | 1 | 2.0 |
| Bisabolol | 1 | 2 |

This formulation was prepared as described above for the 0.2% $CuO_{(1-x)}ZnO_x$ formulation. Antimicrobial activity was similarly tested by the ASTM E2315-16 standard against *Staphylococcus aureus*. After 2 h of contact time, high antibacterial activity of 3 log reduction was observed under both conditions tested (with and without preconditioning).

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method for treating a wound by inhibiting microbial growth in or on the wound in a subject in need thereof comprising contacting a wound on the subject with a therapeutically effective amount of an antimicrobial topical ointment consisting of:
   about 76.2 wt % polyethylene glycol (PEG)-400;
   about 20 wt % PEG-4000;
   about 0.4-1.0 wt % polysorbate-80;
   about 1 wt % caprylic/capric triglycerides;
   about 1 wt % α-Bisabolol; and
   about 1 wt % $CuO_{(1-x)}ZnO_x$,
   wherein the antimicrobial ointment inhibits microbial growth in or on the wound by at least 99%, thereby treating the wound.

2. The method of claim 1, wherein the wound is an incision, acute or chronic surface injury, burn, diabetic ulcer, topical mycosis, infected eczema, or infectious acne.

3. The method of claim 1, wherein the composition inhibits the growth of antibiotic-resistant microbes.

* * * * *